(12) United States Patent
Sauer et al.

(10) Patent No.: US 7,235,086 B2
(45) Date of Patent: Jun. 26, 2007

(54) CRIMPING INSTRUMENT WITH MOTION LIMITING FEATURE

(75) Inventors: Jude S. Sauer, Pittsford, NY (US); Jonathan Gross, Canandaigua, NY (US)

(73) Assignee: LSI Solutions, Inc., Victor, NY (US)

( * ) Notice: Subject to any disclaimer, the term of this patent is extended or adjusted under 35 U.S.C. 154(b) by 346 days.

(21) Appl. No.: 10/423,158

(22) Filed: Apr. 25, 2003

(65) Prior Publication Data

US 2003/0204205 A1 Oct. 30, 2003

Related U.S. Application Data

(63) Continuation-in-part of application No. 09/776,431, filed on Feb. 2, 2001, now Pat. No. 6,997,931.

(51) Int. Cl.
*A61B 17/10* (2006.01)
*A61B 17/08* (2006.01)

(52) U.S. Cl. .............. 606/139; 606/142; 606/144; 606/151

(58) Field of Classification Search ............. 606/139, 606/142, 151, 155, 144; 29/282, 751; 140/76, 140/105, 106, 7; 227/175.1, 175.2, 175.3, 227/175.4, 180.1
See application file for complete search history.

(56) References Cited

U.S. PATENT DOCUMENTS

| | | | |
|---|---|---|---|
| 5,160,339 A * | 11/1992 | Chen et al. ............. 606/158 |
| 5,520,702 A | 5/1996 | Sauer et al. |
| 5,643,289 A | 7/1997 | Sauer et al. |
| 5,669,917 A | 9/1997 | Sauer et al. |
| 5,766,183 A | 6/1998 | Sauer |
| 5,779,130 A * | 7/1998 | Alesi et al. ............. 227/176.1 |
| 5,871,135 A * | 2/1999 | Williamson IV et al. 227/178.1 |
| 5,911,353 A * | 6/1999 | Bolanos et al. ......... 227/180.1 |
| 6,368,334 B1 | 4/2002 | Sauer |
| 6,641,529 B2 * | 11/2003 | Kuranishi ............... 600/160 |
| 2002/0107530 A1 | 8/2002 | Sauer et al. |

* cited by examiner

*Primary Examiner*—Michael J. Hayes
*Assistant Examiner*—Michael G. Mendoza
(74) *Attorney, Agent, or Firm*—Stephen B. Salai, Esq.; Brian B. Shaw, Esq.; Harter Secrest & Emery

(57) ABSTRACT

A surgical crimping instrument for crimping a sleeve including an anvil and a hammer moveable relative to each other to crimp the sleeve, a pusher movable longitudinally and engaging the hammer and/or anvil for urging the hammer and the anvil together as the pusher moves longitudinally from a first position to a second position, and cooperative stops adjacent to the hammer and the anvil for limiting the relative movement of the hammer towards the anvil.

32 Claims, 17 Drawing Sheets

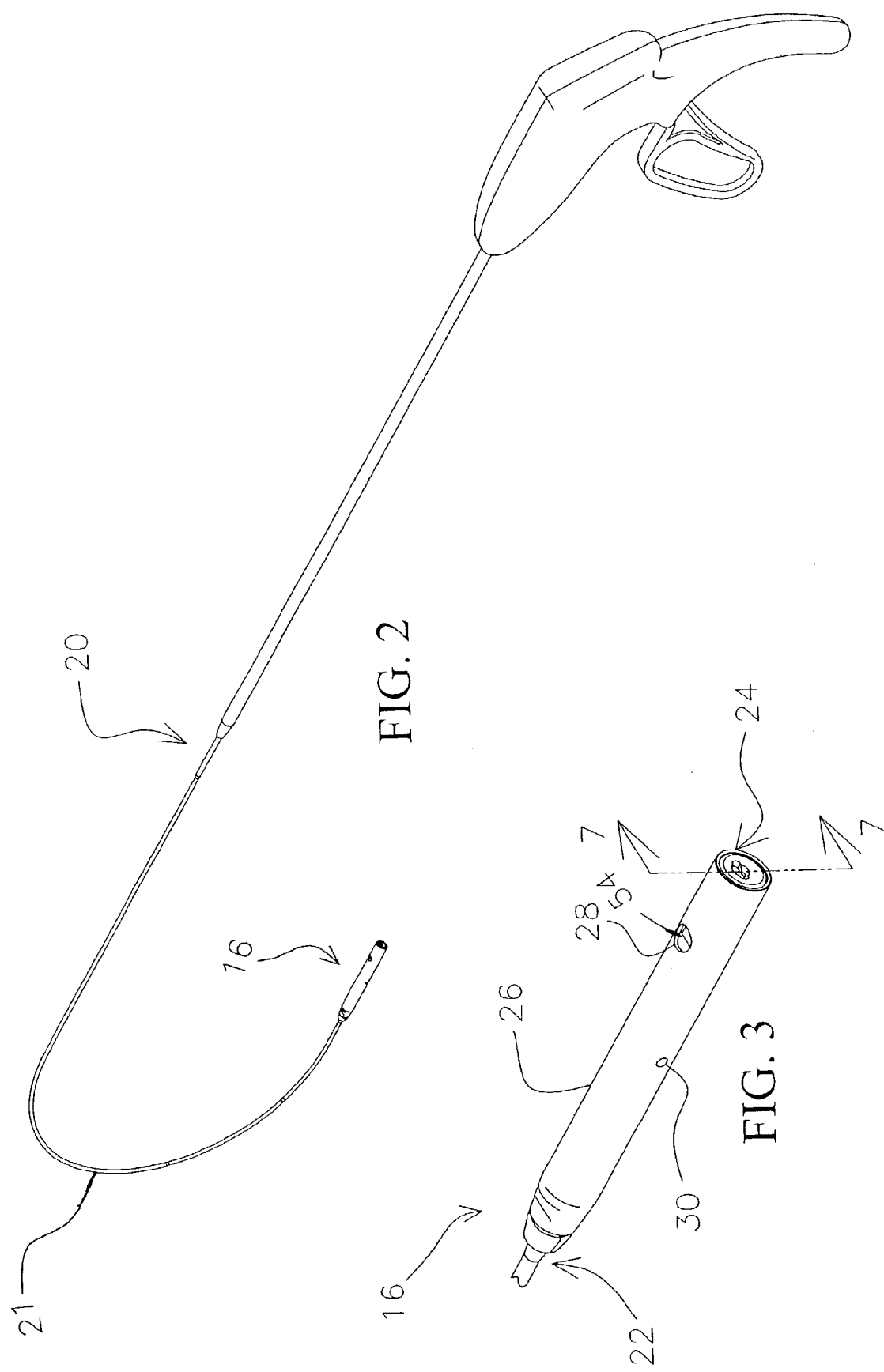

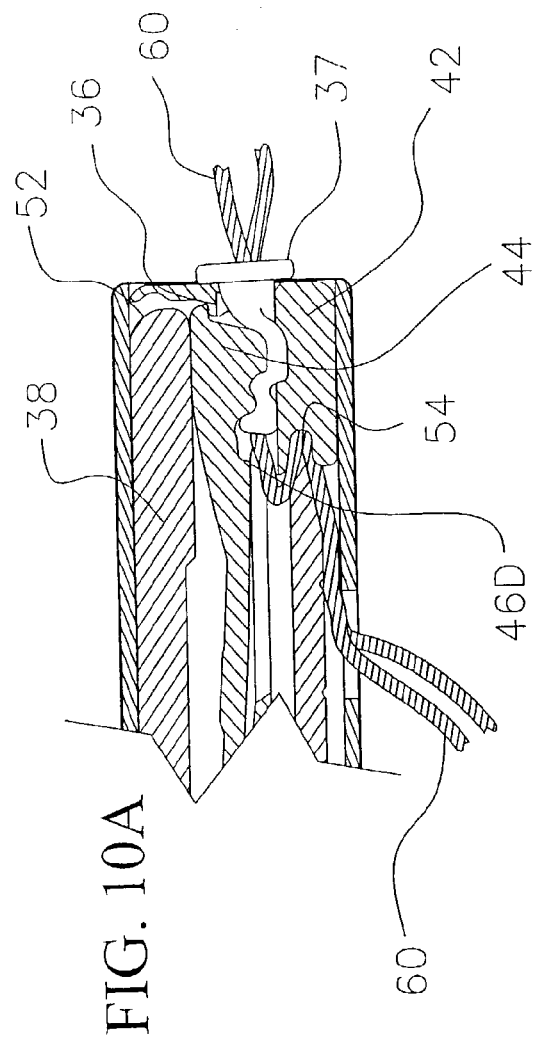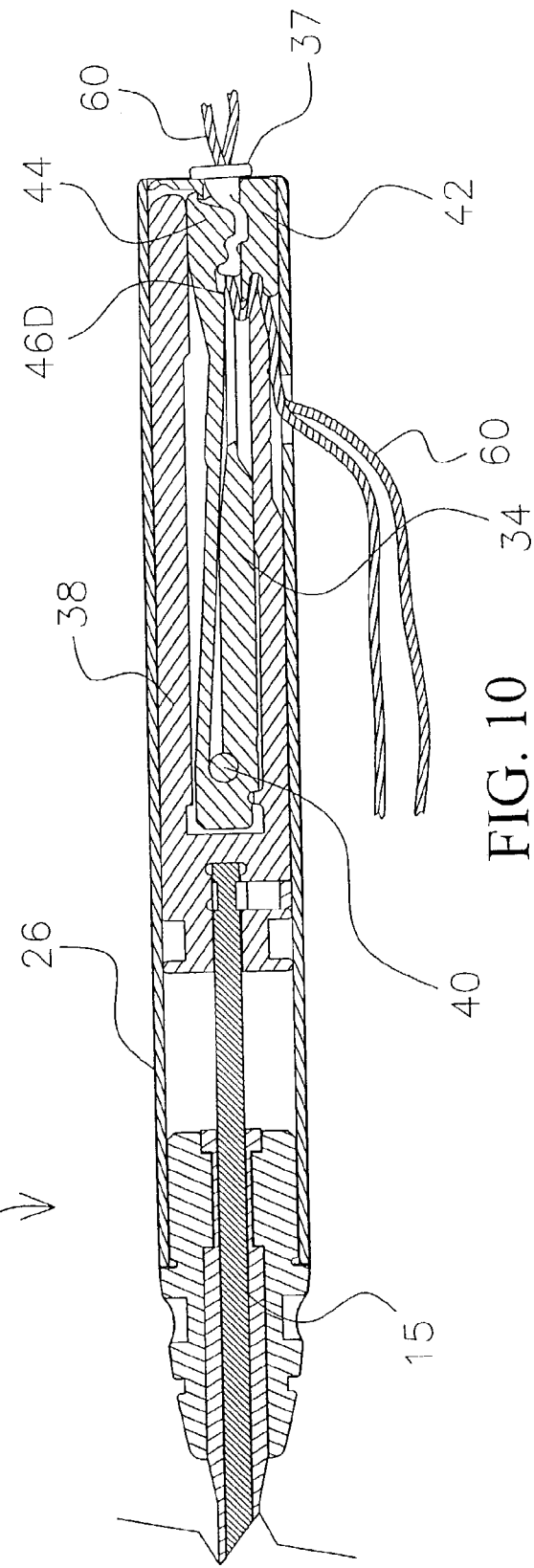

CRIMPING INSTRUMENT WITH MOTION LIMITING FEATURE

CROSS-REFERENCE TO RELATED APPLICATIONS

This application is a continuation in part of application Ser. No. 09/776,431 now U.S. Pat. No. 6,997,931, Publication Number 20020107530, entitled "SYSTEM FOR ENDOSCOPIC SUTURING," filed Feb. 2, 2001.

BACKGROUND OF THE INVENTION

1. Field of the Invention

This invention relates generally to surgical instruments, and more particularly, to a surgical instrument for crimping a sleeve to a secured suture that is more easily manufactured than instruments heretofore known.

2. Background Art

Malleable sleeves such as the sleeves sold under the trademark Titanium Knot by LSI Solutions are a significant improvement over hand or instrument-tied knots in laparoscopic surgical procedures. The sleeves, which are made of a malleable material compatible with prolonged exposure to body tissue are slid over two or more strands of suture and deformed or crimped to secure the strands of suture.

An example of an instrument for crimping a sleeve of the type described is shown in U.S. Pat. No. 6,368,334, entitled "VASCULAR HOLE CLOSURE." The crimper shown in the patent deforms the sleeve between two relatively moveable jaws when a lever on the instrument is squeezed toward the handle. The instrument described performs its function satisfactorily but is demanding to manufacture.

It is desirable to impart just enough, but not too much, pressure on the sleeve to deform it to a desired extent. If the sleeve is insufficiently deformed, the sutures may slip, and if the sleeve is deformed too much, it may be weakened and not secure the sutures for as long as is intended.

Known crimping instruments rely on the accurate manufacture of the relatively movable parts to establish the extent to which the sleeve will be crimped. Also, in known crimping instruments, the distance a pusher rod moves to force the jaws on which the hammer and anvil are disposed together affects the amount of crimp. This creates the possibility that, if the tolerances are not exact, or the surgeon does not completely squeeze the actuating handle to the lever, the sleeve may be incompletely crimped and may slip, or may be over crimped and weakened.

While a large number of crimpers in accordance with the prior art have been made, the cost of maintaining the manufacturing tolerances necessary to insure that these crimpers perform adequately, has been high. There is a need for an improved crimper that continues to perform as well as the existing crimpers, but which can be made without the need for maintaining the manufacturing tolerances for the parts and assembly at the very high levels required by the existing designs.

It is an object of this invention to provide a crimper for surgical suturing operations that overcomes the disadvantages of crimpers heretofore known.

It is another object of this invention to provide a crimper that is easy to manufacture, and at the same time, retains or improves on the crimping quality of crimpers heretofore known.

BRIEF SUMMARY OF THE INVENTION

Briefly stated and in accordance with a presently preferred aspect of the invention, an instrument or "crimper" for crimping a sleeve to a surgical suture includes an anvil having a recess for receiving the sleeve to be crimped, a hammer moveable relative to the anvil to crimp the sleeve, a pusher movable longitudinally and engaging the hammer for urging the hammer and the anvil together as the pusher moves longitudinally from a first position to a second position, and cooperative stops adjacent to the hammer and the anvil for limiting the relative movement of the hammer towards the anvil.

In accordance with another aspect of the invention, the cooperating stops act to prevent further movement of the hammer towards the anvil after the pusher reaches an intermediate position between the first position and the second position, so that the hammer and anvil are brought into the desired degree of opposition without the need for precisely controlling the movement of the pusher.

In accordance with another aspect of the invention, the pusher also includes a cutting blade for cutting a suture.

In accordance with another aspect of the invention, the cutting blade cuts the suture as the pusher moves from the intermediate position to the second position.

In accordance with another aspect of the invention, the hammer and anvil are formed at the ends of two legs of a resilient member which resiliently bias the anvil and hammer apart until squeezed together by the pusher.

In accordance with another aspect of the invention, the pusher engages at least one of the first and second legs and urges them together to bring the hammer and anvil into opposition and to crimp a sleeve disposed therebetween.

In accordance with another aspect of the invention, the instrument includes a second pair of opposing stops adjacent to hammer and anvil, the hammer and anvil being disposed between the first and second pairs of stops.

In accordance with another aspect of the invention, an opening is provided in one of the first and second legs for passing a suture therethrough.

In accordance with another aspect of the invention, the cutter is disposed on the opposite side of the opening from the sleeve.

BRIEF DESCRIPTION OF THE SEVERAL VIEWS OF THE DRAWINGS

FIG. 2 shows the crimping instrument attached to a surgical instrument with a flexible extension;

FIG. 3 is a prospective view of the crimping instrument in accordance with the present invention;

FIG. 10 is a cross-sectional diagram of the driver-cutter in a second position;

FIG. 10A is an expanded diagram of a portion of FIG. 10;

FIG. 12A shows a partial cutaway of the crimping instrument;

DETAILED DESCRIPTION OF THE INVENTION

Figure 1:
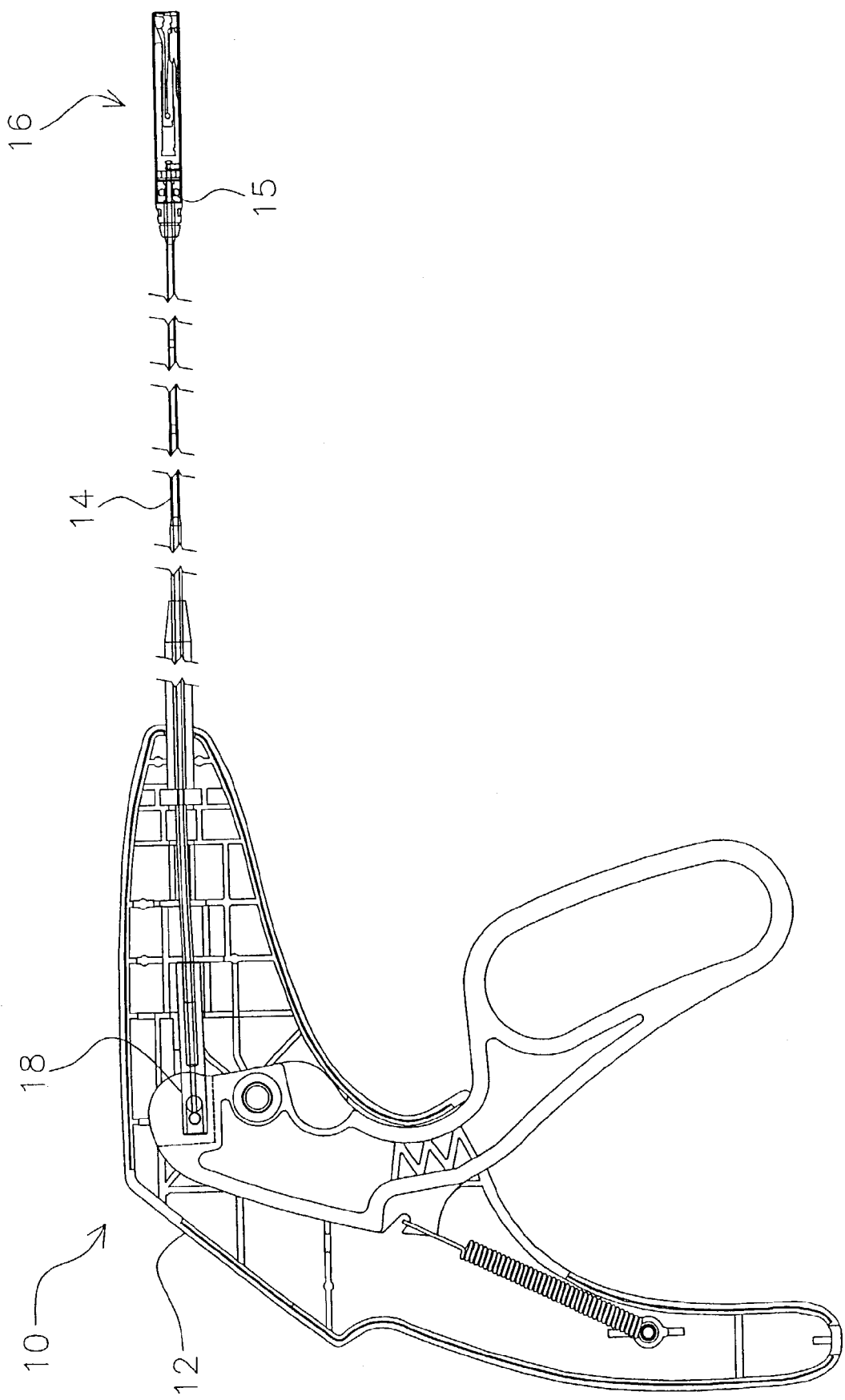
FIG. 1 shows a cross-sectional diagram of a surgical instrument, including the crimping instrument.

FIG. 1 shows an improved suture-securing instrument 10, sometimes referred to as a crimper or crimping instrument, for use in many applications, including endoscopic surgery of the types described in co-pending application entitled SYSTEM FOR ENDOSCOPIC SUTURING by the Applicant, publication No. 20020107530A1 filed Feb. 2, 2001. This surgical instrument is shown with a handle 12 for attaching a guide tube 14, or other support, a driver 15, and a crimping end 16. The driver shown in FIG. 1 is a sleeve with a cable in it. While applicant has shown one type of driver, it will be understood that the invention is not limited to this type of driver. Any other driver capable of moving the crimping end. The crimping end can be integrated with many different instruments. The crimping end 16 may be detachable from the tube 14, or other support, if necessary. The crimping instrument can be used in conjunction with suturing instruments such as the SEW-RIGHT™ suturing instrument manufactured by LSI Solutions, Inc. Rochester, N.Y. The handle 12 may be shaped like a pistol grip having a handle portion and an actuator member 18 to allow the driver 15 to move longitudinally. An example of such a handle is described in the co-pending patent application Ser. No. 09/776,431.

During endoscopic surgery a suturing instrument is used to place one or more sutures in a target area of tissue. The two ends of the suture are secured by a suture securing instrument, such as the one described herein. The crimping instrument of this invention uses the crimping end 16 to secure the sutures. While the applicant will discuss the crimping instrument in reference to endoscopic surgery, there are other uses of the crimping instrument during surgery. It can be used whenever a sleeve is to be crimped, in both human and animal surgeries.

FIG. 2 shows the crimping end 16 attached to a surgical instrument 20 with an elongated flexible extension 21.

FIG. 3 is an enlarged perspective view of the crimping end of the instrument shown in FIG. 2. A first end, referred to as the proximal end because it is close to the operator, is secured to an end of the flexible extension 21 by a tapered connector 22. The details of this connection are shown in U.S. Pat. No. 6,368,3334, mentioned above. The crimping end of 16 has an elongated tubular body 26 terminating in a second end 24 referred to as the distal end because it is located the furthest from the operator. The distal end 24 has a generally flat face with an opening therein for receiving a sleeve to be crimped. The ends of the suture extending through the sleeve to be crimped are led through the interior of cylindrical housing 26 and out opening 28. The end portion of a cutting edge 54 described in more detail in connection with FIG. 6 and the seen-through opening 28. A pin 30 extends through the housing and secures crimper 34, as shown and described in more detail in connection with FIG. 4. A section of crimping end 16 taken along line 7-7 is shown in FIG. 7.

While the crimping end is shown in a cylindrical housing, it will be recognized that the housing may take other forms and have other shapes consistent with the manner in which the crimper is to be used. The housing may depart from a strictly cylindrical shape and may be oval, have flat sides, have a larger or fewer number of openings, may comprise a cage, or generally take any other form that supports the various elements thereof as will be described in more detail below.

Figure 4:
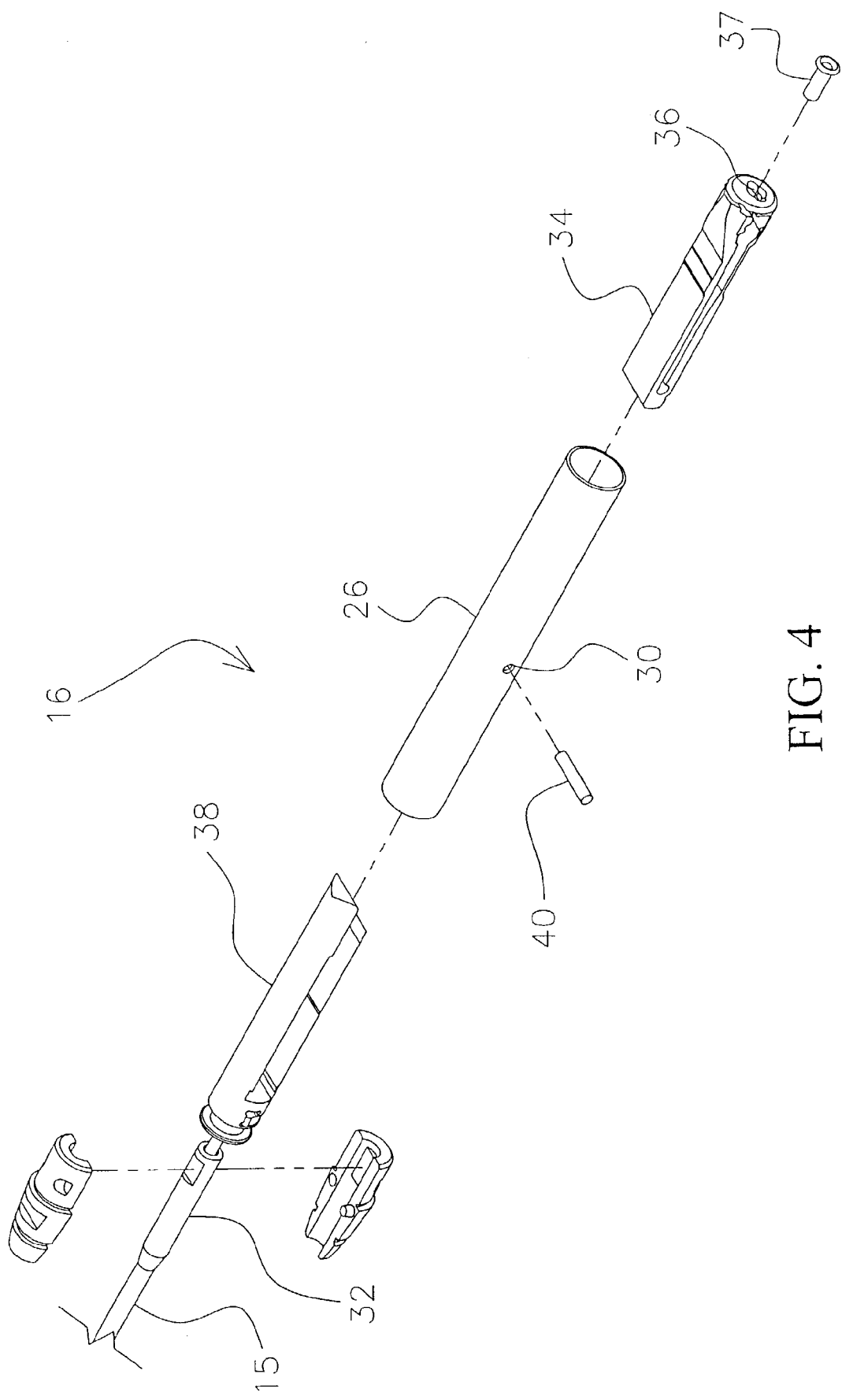
FIG. 4 is an exploded view of the crimping instrument of FIG. 3.

FIG. 4 is an exploded perspective diagram of the crimping end 16 showing the driver 15 with an attachment end 32. The crimping end 16 having a crimper 34 with a recess 36 for receiving a sleeve 37 to be crimped, hereafter referred to as the crimping sleeve 37. The crimping end 16 also has a pusher, hereafter referred to as a driver-cutter 38, moveable relative to the crimper 34. The crimper has a recess 36 for receiving the crimping sleeve. The crimper 34 is held in the body 26 by a pin 40. The recess 36 is for receiving the crimping sleeve 37 such as a TITANIUM KNOT™ sleeves (not shown) manufactured by LSI Solutions, Inc. of Rochester, N.Y.

Figure 5:
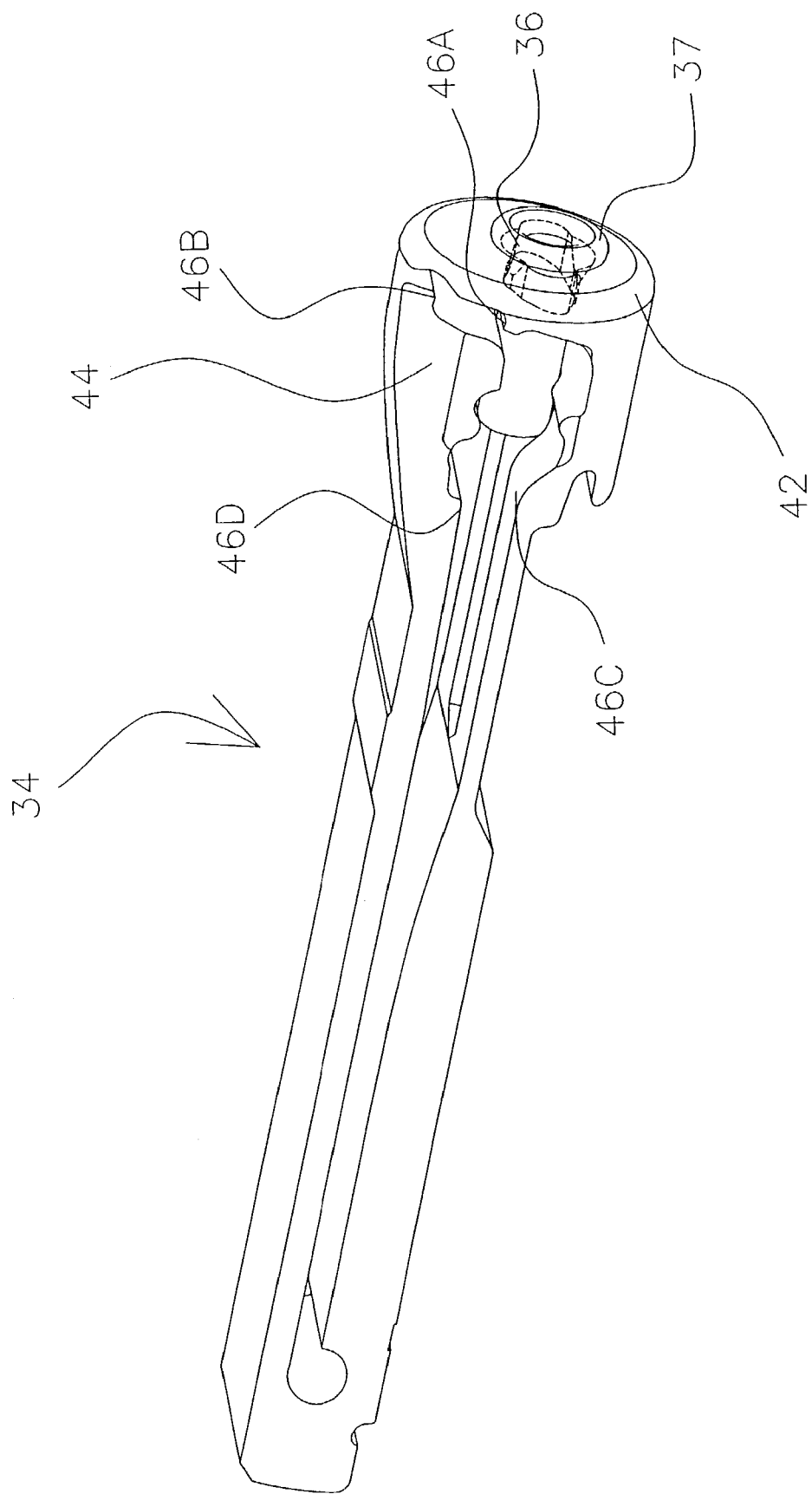
FIG. 5 is a perspective view of the resilient crimper of the crimping instrument.

The crimper 34, shown on FIG. 5, is a resilient crimper 34 which has an anvil 42 and a hammer 44 on two opposing legs with a separating gap in the normal configuration, also known as a "resting" position. While applicant refers to an anvil and a hammer because these are convenient descriptive terms, it will be understood that the invention is not limited to the particular elements shown. Applicant intends hammer and anvil to denote any two relatively moveable members capable of deforming the sleeve 37 placed therebetween and securing the ends of a suture disposed in the sleeve 37 when the two elements are brought together. While applicant refers to a resilient crimper, other crimpers that are spring-loaded, hinged, or other arrangements that would allow the two legs to be urged apart a sufficient amount to insert a sleeve 37 between the legs and brought together to crimp the sleeve, would work just as well in this invention. The crimper could also be a unitary resilient crimper in certain circumstances where there are effectively no legs.

The resilient crimper 34 has one or more cooperating stops 46 that determine the range of movement of the legs of the resilient crimper 34. These cooperating stops 46 precisely control the extent that the crimping sleeve 37 is crimped onto the suture. This embodiment of the invention shows primary cooperating stops 46A (on anvil) and 46B (on hammer) and secondary cooperating stops 46C and 46D. Both primary 46A and 46B and secondary stops 46C (on anvil) and 46D (on hammer) precisely control the crimping of the crimping sleeve 37 by precisely defining the crimping positions of the legs of the resilient crimper 34 as the sleeve is crimped and the sutures are cut.

Figure 6:
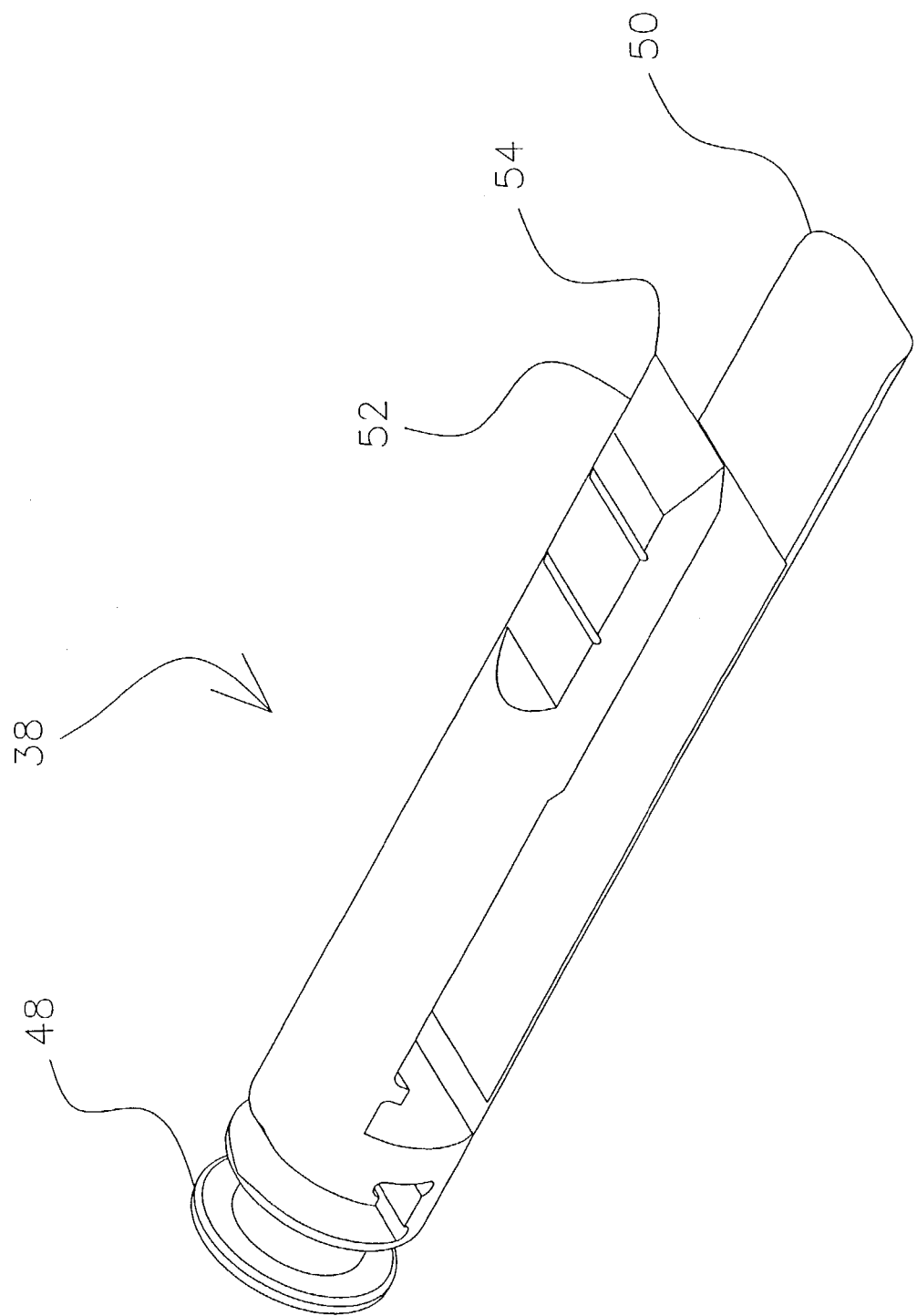
FIG. 6 is a perspective view of the driver-cutter of the crimping instrument.
Figure 7:
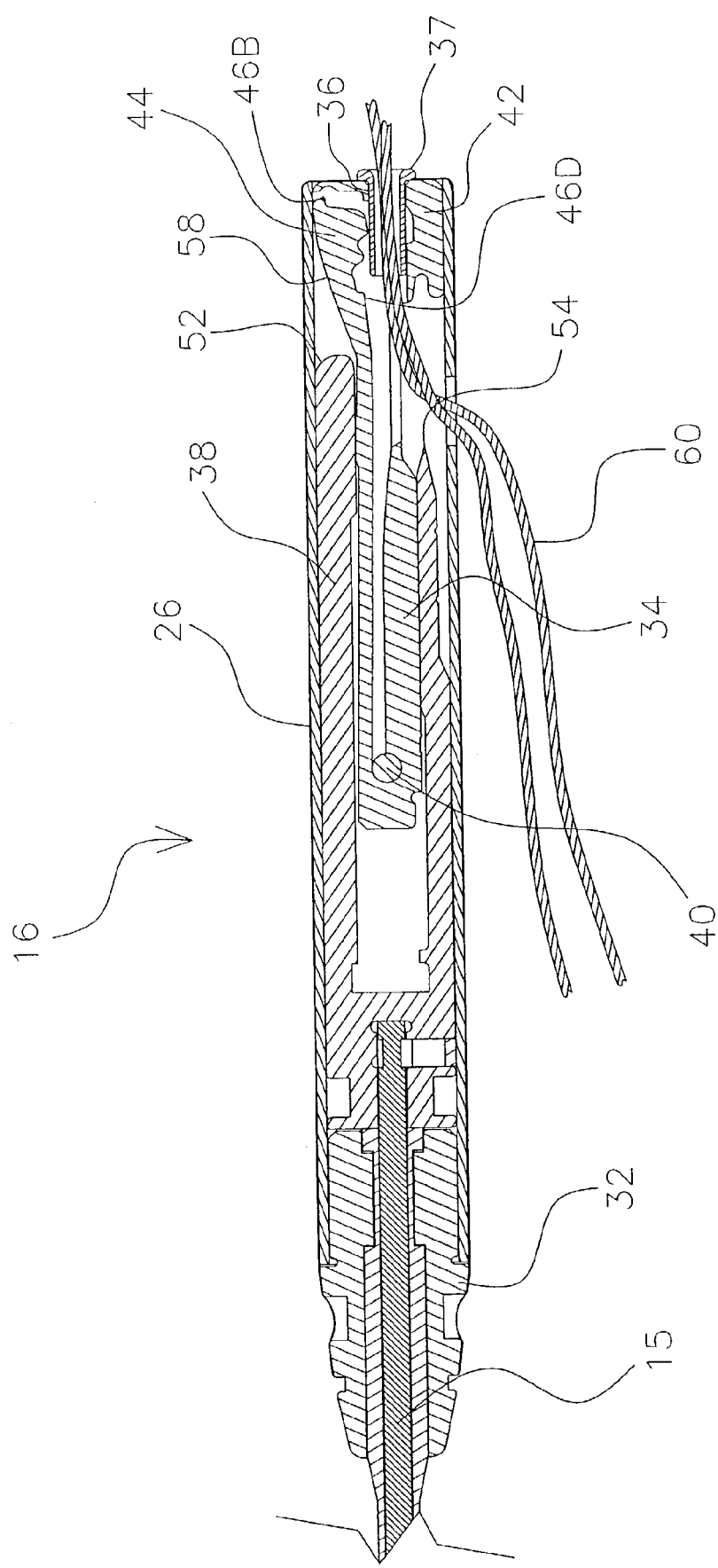
FIG. 7 is a cross-sectional diagram of the system of FIG. 3 along lines 7-7 of FIG. 3 with a crimping instrument in the first position.

FIG. 6 shows a driver-cutter 38 with a connector 48 and a blunt distal end 50. The driver-cutter 38 also has a sharp distal end 52 with a sharp cutting edge 54. The driver-cutter 38 concentrically contains the resilient crimper 34 such that the blunt distal end 50 abuts the hammer 44. The driver-cutter 38 engages the crimper leg members and urges them together to bring the hammer 44 and the anvil 42 into opposition sufficient to crimp the sleeve disposed in recess 36. The sharp cutting edge 54 acts as a cutting blade for cutting the suture after it has been secured by the crimping sleeve 37 inserted in the recess 36, as shown in FIG. 5.

While applicant refers to a pusher and a driver-cutter, other drivers such as one without a cutter, one that pulls instead of pushes, or one that urges with shoulders instead of the blunt portion and cuts with another sharp edge would work also as long as the driver and the resilient crimper move relative to each other.

FIG. 7 shows a cross-sectional diagram of the crimping instrument 16 with the driver-cutter 38 cooperatively surrounding the resilient crimper 34. The resilient crimper is in the first or "resting" position with the hammer 44 at rest relative to the anvil 42 and the crimping sleeve 37.

Figure 8:
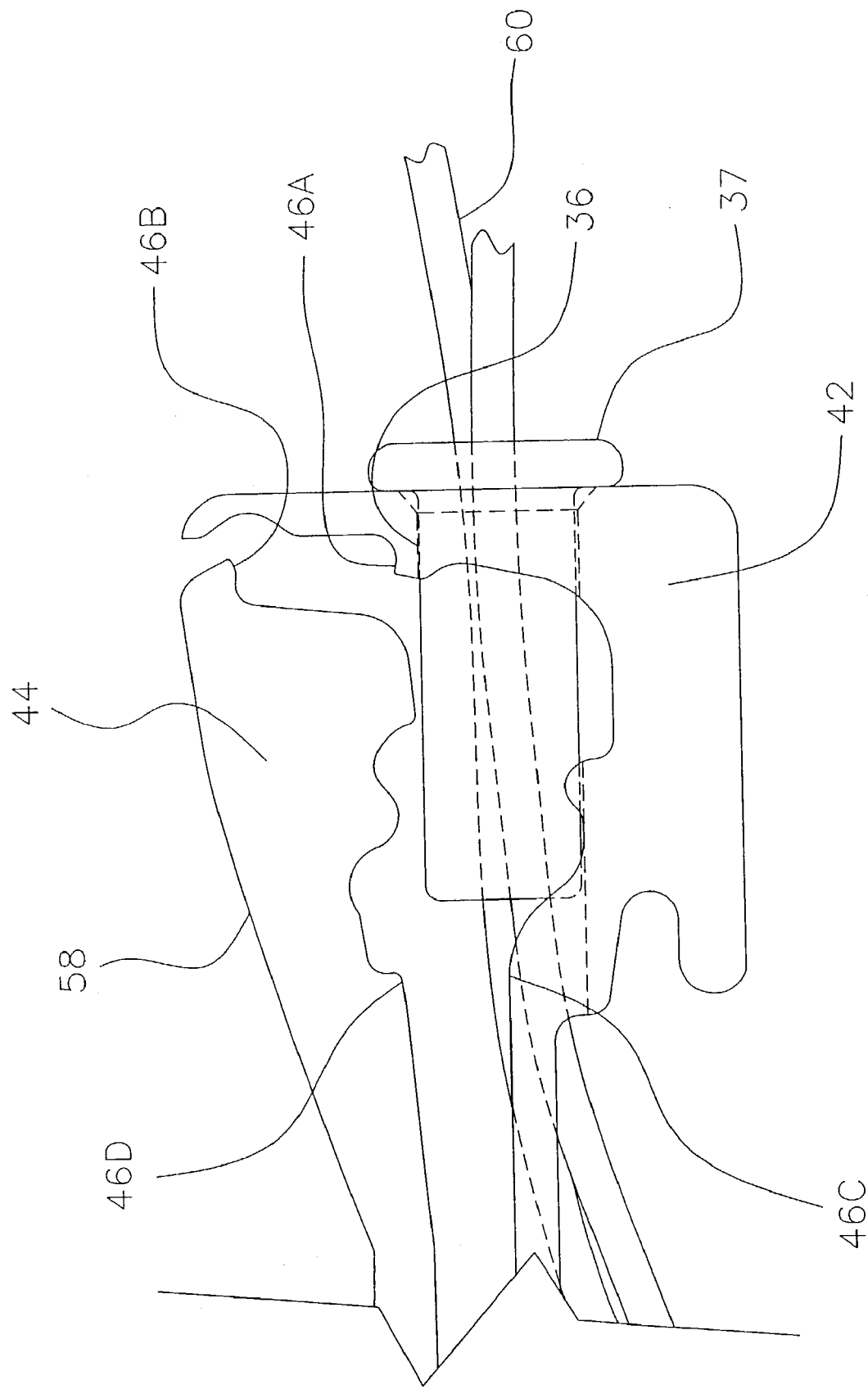
FIG. 8 is an expanded view of the end portion of the resilient crimper of the crimping instrument at rest.

FIG. 8 shows an expanded cross-sectional view of the end of the resilient crimper 34 in the resting position. The primary cooperating stops 46A and 46B, and the secondary cooperating stops 46C and 46D, are clearly shown.

Figure 9:
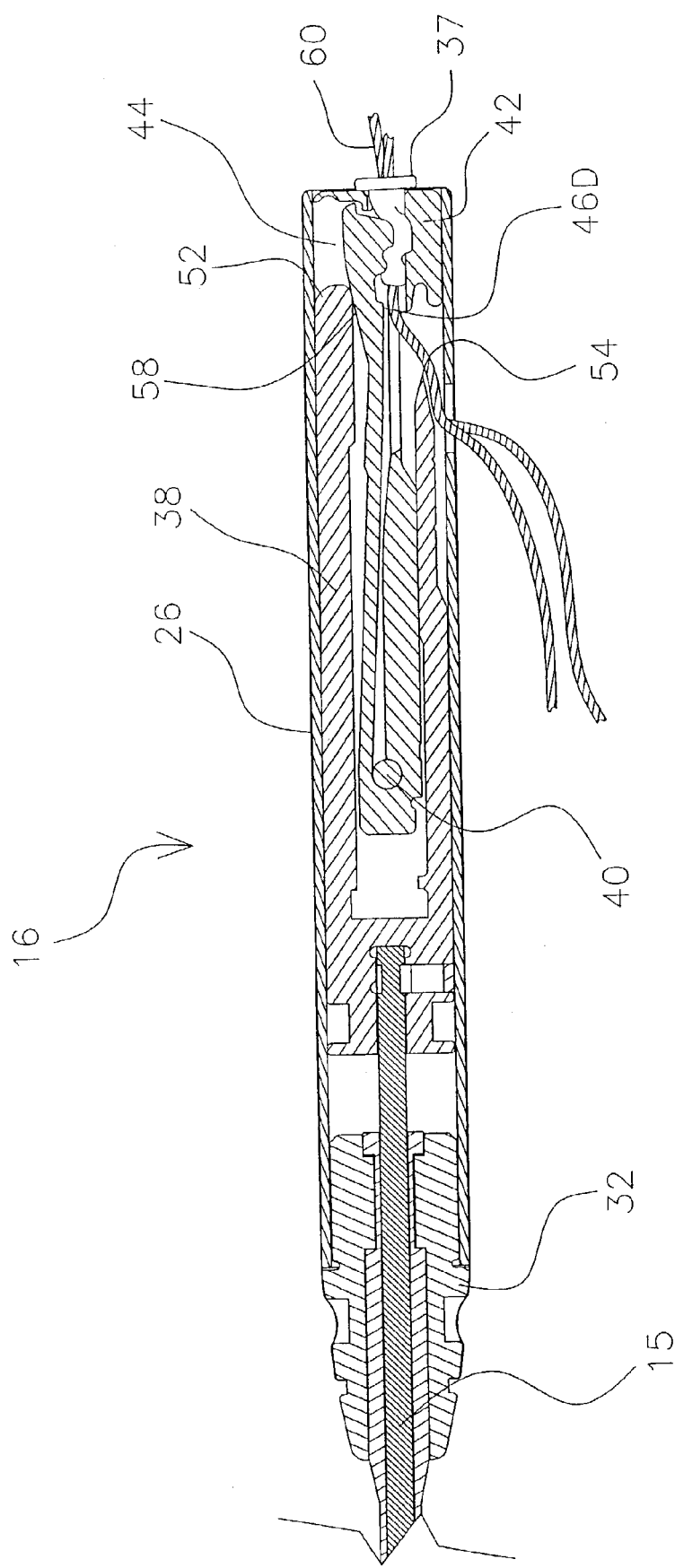
FIG. 9 is a cross-sectional diagram of the crimping instrument in an intermediate position.

FIG. 9 shows the resilient crimper 34 in an intermediate position as the hammer 44 is being moved toward the anvil 42 by the blunt distal end 50 as it encounters a ramp 58. The movement is terminated by the primary cooperating stops 46A and 46B making contact. This results in the hammer 44 being in close proximity to the anvil 42 such that the crimping sleeve 37 is deformed.

FIGS. 10 and 10A show the resilient crimper 34 in a second position where the crimping sleeve 37 has already been deformed sufficiently to secure one or more sutures 60 and the sutures have been cut by the sharp cutting edge 54. The sutures 60 enter from the tissue, through the crimping sleeve 37 as shown in the exploded detail of the end of the crimper. The secondary cooperating stops 46C and 46D have also made contact in this situation and the sutures 60 are cut.

Figure 11:
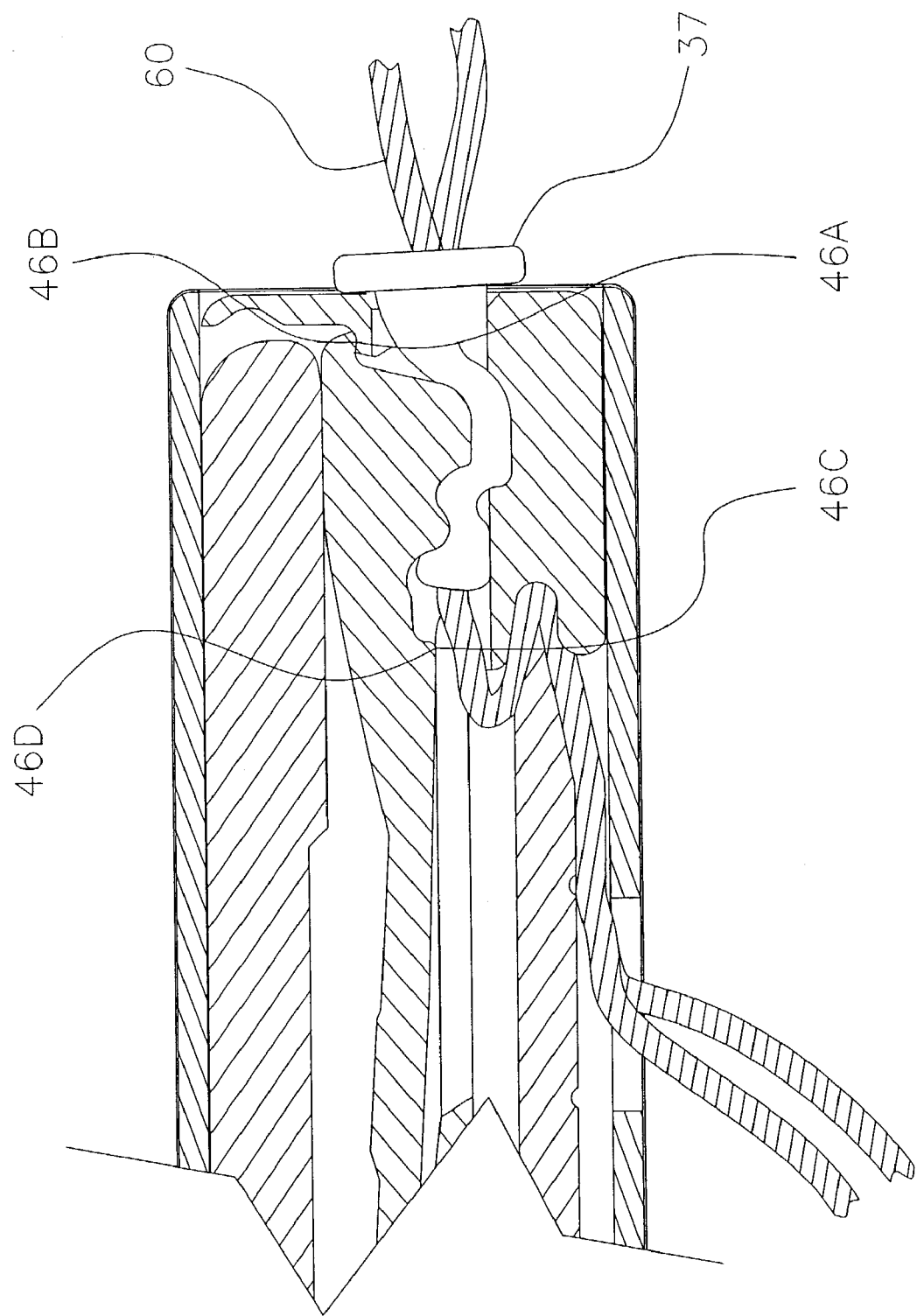
FIG. 11 is an expanded view of the driver-cutter in the second position.

FIG. 11 shows an expanded, cross-sectional view of the end of the resilient crimper in the second position. The primary cooperative stops 46A and 46B, and the second cooperative stops 46C and 46D, are clearly shown.

While this embodiment of the invention uses two pairs of cooperating stops, a single pair of stops, or one or more stops on only one of the anvil or hammer, engaging the other element directly, may be employed consistent with the invention. What is important is that the stop or stops control the extent of deformation of the sleeve without relying on the precise size or position of an actuating element that engages the legs of the crimper. In this embodiment the primary cooperating stops precisely control the distance the resilient crimper moves before deforming the sleeve. The secondary stops provide a means of further controlling movement which may result from the residual spring force from the resilient crimper after the primary stops have made contact or from other sources. The newer soft titanium sleeves are more sensitive to displacement distances so the combination of the primary and secondary stops is particularly effective in protecting these softer sleeves.

While the applicant refers to using the cooperating stops to precisely control the distance the resilient crimper moves before deforming the sleeve, these stops can also control movement after the stops have stopped movement at the end of the crimper or along the crimper with the secondary stops allowing further movement before the second position is reached. One of the primary and/or secondary stops can also be used for other purposes, particularly securing the sutures prior to cutting them.

Figure 12:
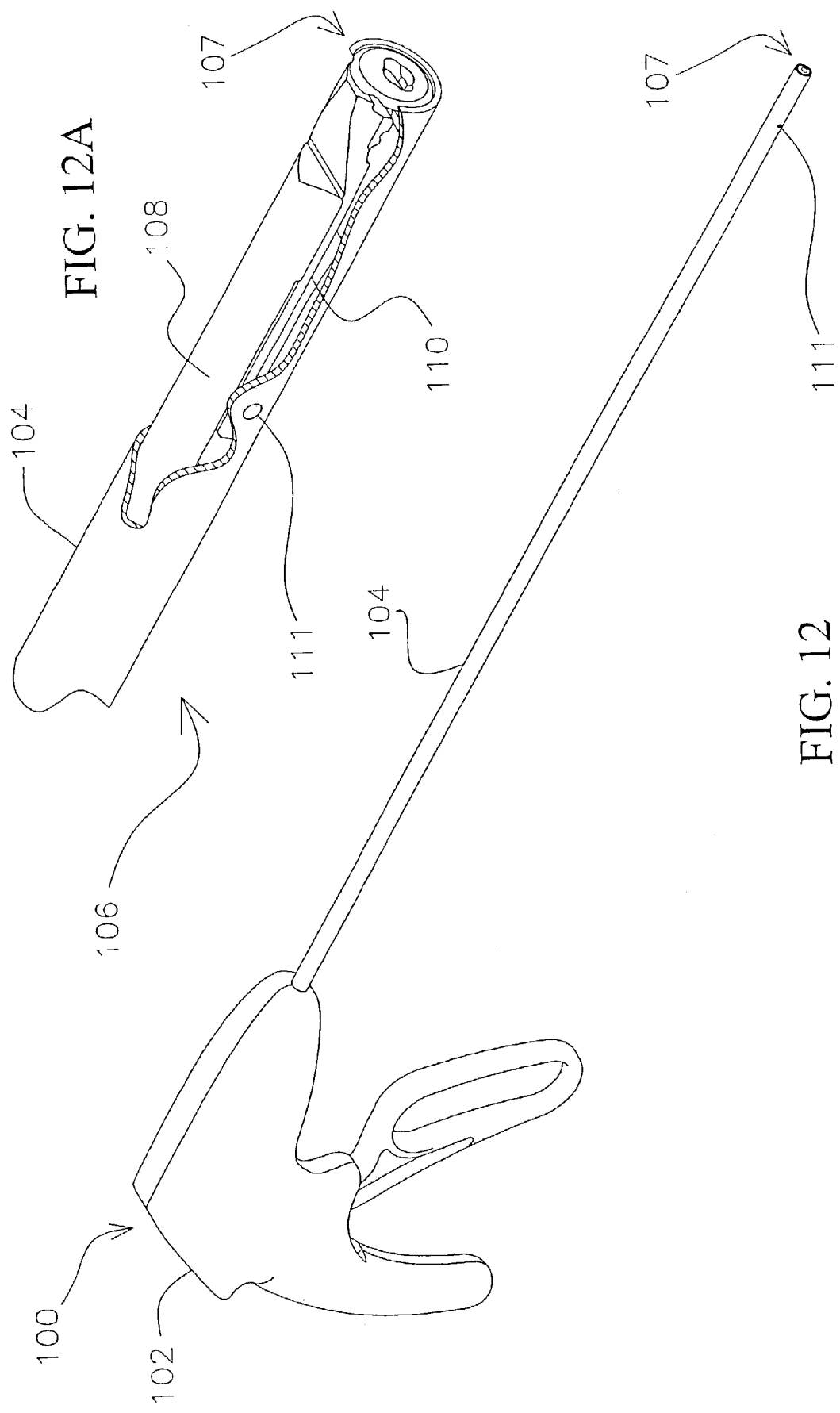
FIG. 12 shows another embodiment of a surgical instrument containing the crimping instrument.

FIG. 12 shows another embodiment of a crimping instrument 100 with a handle 102 and tubular body 104 attached to a crimping end 106.

FIG. 12A is a perspective view of the crimping end 106 showing a distal end 107 for tubular body 104. Also shown in the tubular body 104 is a driver-cutter 108, a resilient crimper 110, and an opening 111.

Figure 13:
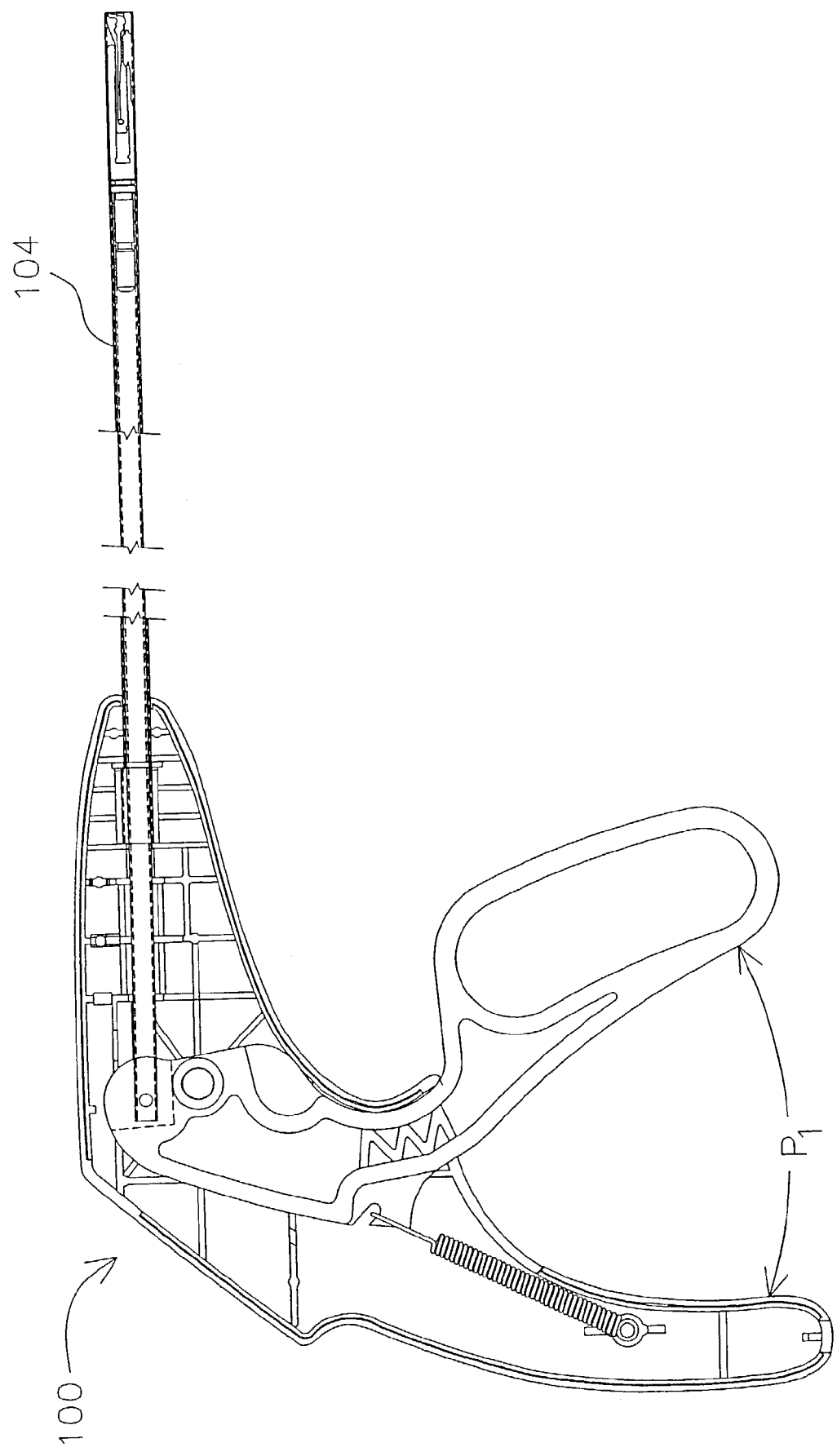
FIG. 13 is a cross-sectional view of the surgical instrument of FIG. 12, including the crimping instrument for securing a suture.

FIG. 13 shows the lever in a resting position ($P_1$) before the crimper is activated. The resilient crimper is in a rest position at this time.

Figure 14:
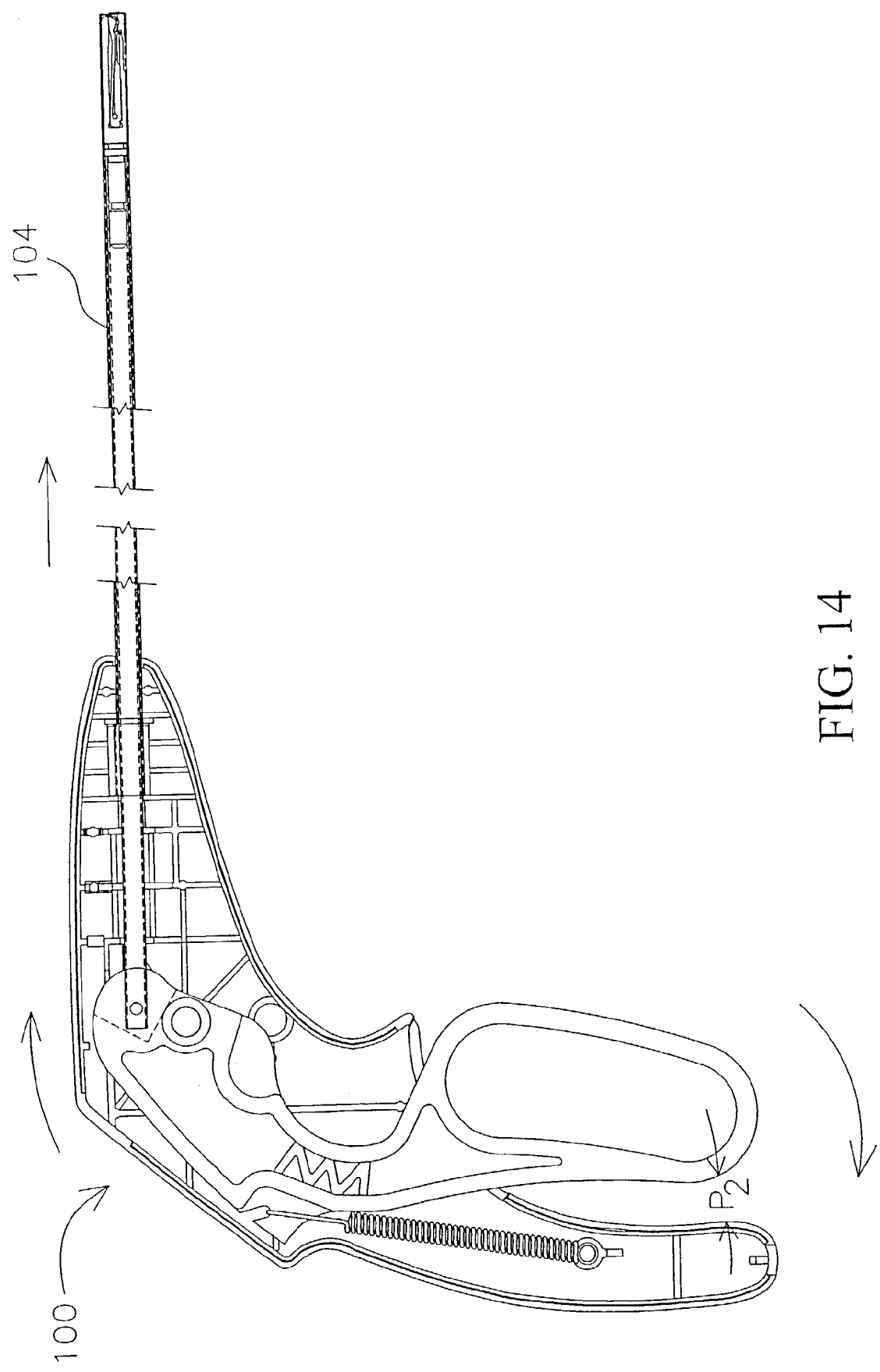
FIG. 14 is a cross-sectional diagram of the surgical instrument of FIG. 12, showing the handle being activated to move the crimping instruments from a first position to a second position.

FIG. 14 shows the lever in an activated position ($P_2$) when the resilient crimper has been moved to deform the sleeve as well as secure and cut the sutures.

Figure 15:
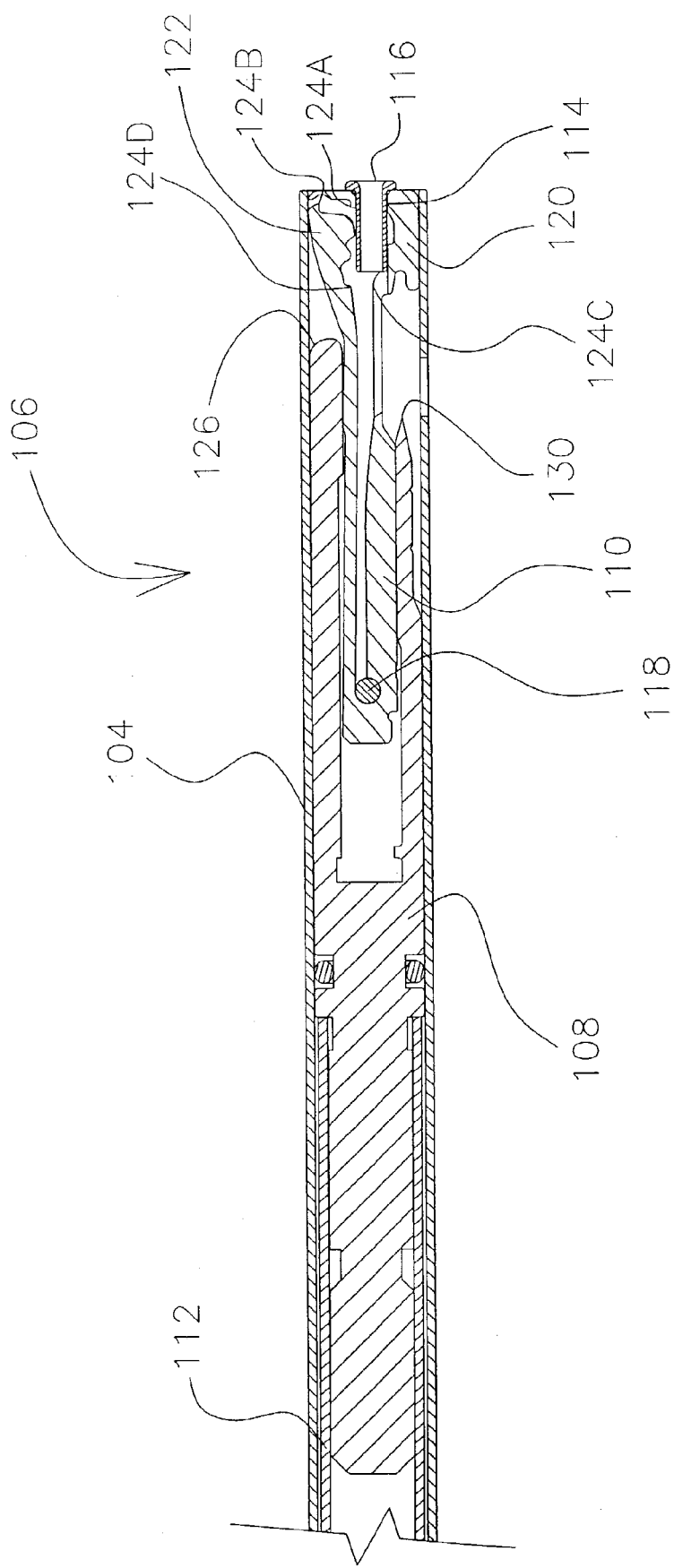
FIG. 15 is a cross-sectional diagram of the system of FIG. 12, showing the resilient crimper at rest.

FIG. 15 is a cross-sectional diagram of the crimping end 106 showing a driver 112 which is a tube in this embodiment. The resilient crimper 110 of the crimping end 106 has a recess 114 for receiving a sleeve 116 to be crimped (also referred to as the crimping sleeve 116). Also shown is the pusher, also known as the driver-cutter 108, which can move relative to the resilient crimper 110. The unitary resilient crimper is held in the tubular body 104 by a pin 118 which is inserted into opening 111. The recess 114 can receive any crimping sleeve 116 such as the TITANIUM KNOT® sleeve manufactured by LSI Solutions, Inc. of Rochester, N.Y.

The unitary resilient crimper 110, shown on FIG. 15, has an anvil 120 and a hammer 122 on two opposing legs with a separating gap in the normal configuration, also known as a "resting" position. The resilient crimper 110 has one or more cooperating stops 124 that determine the range of movement of the legs of the resilient crimper 110. These cooperating stops 124 precisely control the extent that the sleeve is crimped onto the sutures. This embodiment of the invention shows primary cooperating stops 124A (on anvil) and 124B (on hammer) and secondary stops 124C and 124D. The stops 124 precisely control the crimping of the sleeve by precisely defining the crimping positions of the legs of the resilient crimper 110 as the sleeve is crimped and the sutures are cut.

Figure 16:
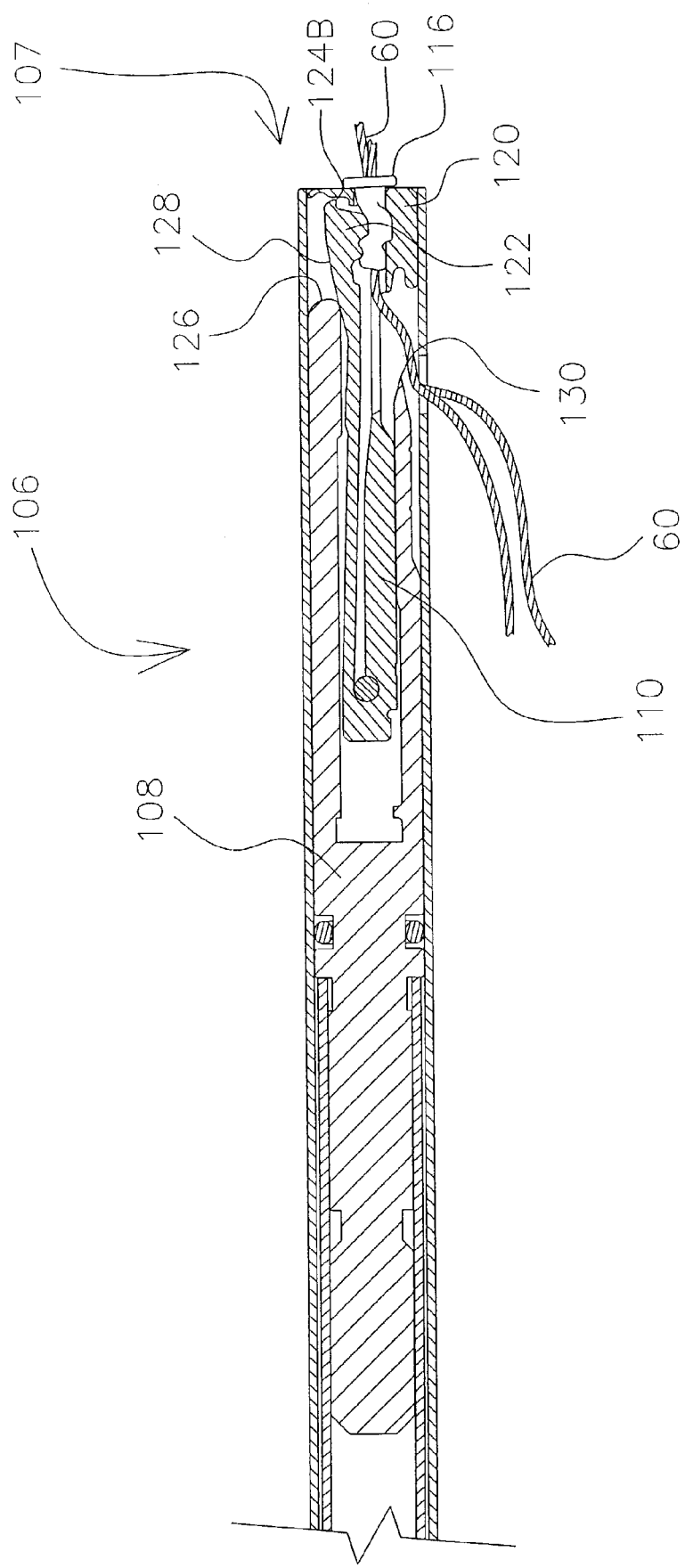
FIG. 16 shows the driver-cutter starting to move in relation to the resilient crimper.

FIG. 16 shows the driver-cutter 108 moved toward the distal end 107, as the handle is partially activated. A blunt portion 126 of the driver-cutter 108 is abutting an incline surface 128 on the hammer.

Figure 17:
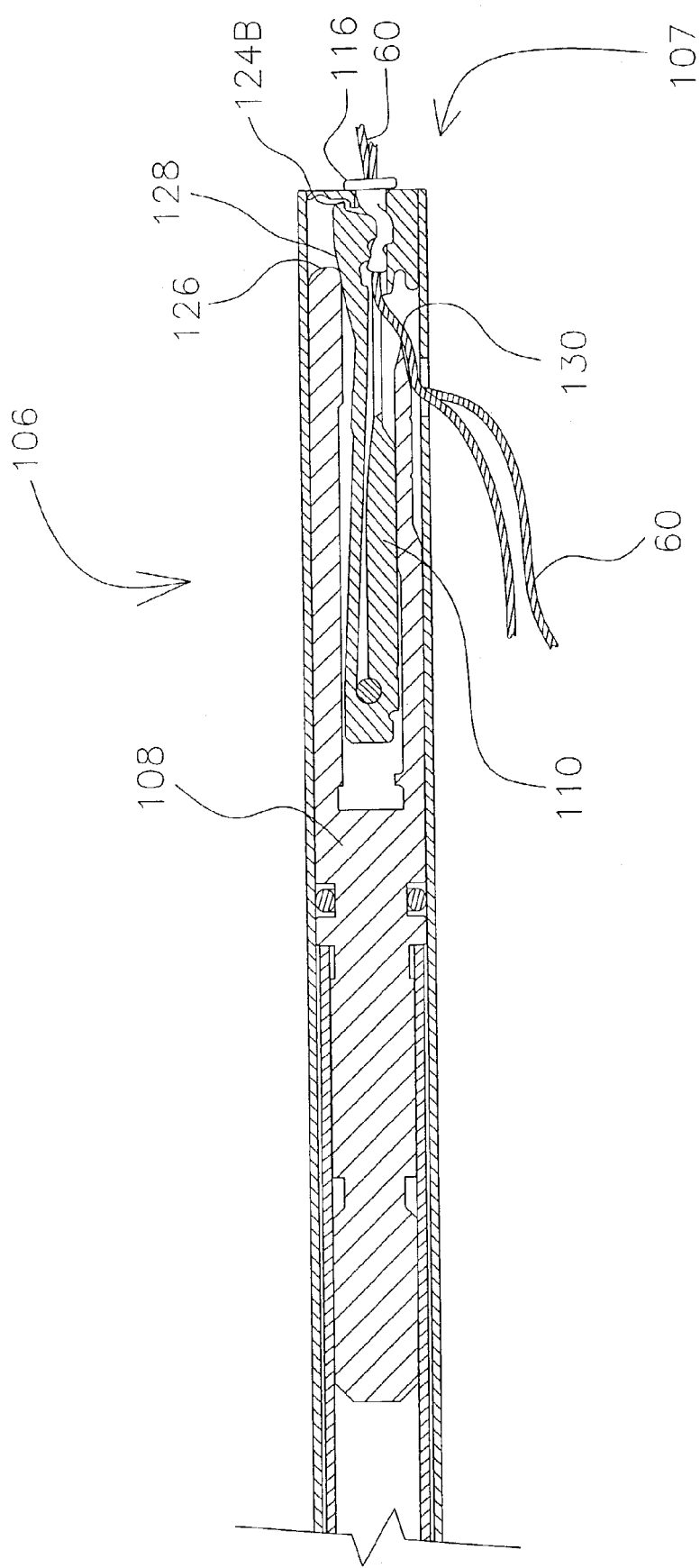
FIG. 17 shows the resilient crimper in an intermediate position.

FIG. 17 shows the resilient crimper 110 in an intermediate position where the two legs have moved together as the blunt portion 126 moves up the incline surface 128 of the unitary resilient crimper 110 an amount sufficient to cause the primary stops 124A and 124B to contact. The crimping sleeve 116 has been deformed to secure the sutures.

Figure 18:
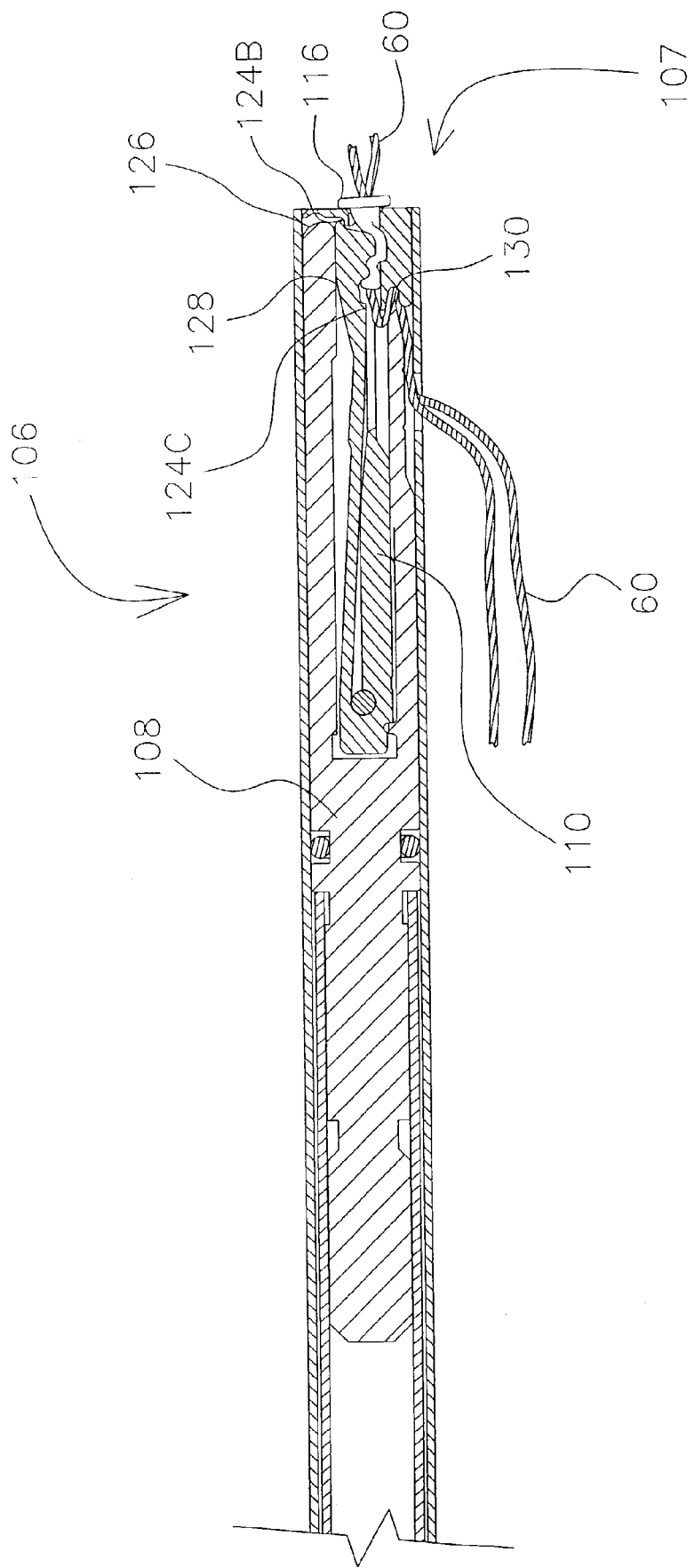
FIG. 18 shows the resilient crimper in a second position.

FIG. 18 shows the resilient crimper 110 in a second position where the crimping sleeve 116 has been deformed sufficiently to secure the sutures and the sutures have been cut by the sharp cutting edge 130 (see FIG. 17).

This crimping instrument can be used in conjunction with other endoscopic instruments in surgeries such as gastrointestinal endoscopic surgery. In gastrointestinal endoscopic surgery, a gastroscope and attached accessory tube can be inserted through the mouth, down the esophagus into the stomach where the suturing will take place. The suturing instrument with a loop of suture loaded is inserted into the accessory tube via cannula until the distal end of the instrument passes through the attachment tip. The tissue engaging end of the suturing instrument is viewable to the operator on the gastroscope display and when the target area of the tissue is located, the tissue is sewn through the sew tip as described in co-pending application Ser. No. 09/776,431 (Publication No. 20020107530). Once the sew tip is lifted, it leaves the suture extending through the tissue as described in the co-pending application.

A suture-securing instrument can then be inserted into the accessory tube with gentle attention applied to the free ends of the loop of the suture. The distal end of the suture securing instrument passes through the attachment tip and is now located near the suture loop extending from the tissue that has just been sutured. The suture securing instrument is positioned adjacent to the tissue, and the crimping instrument is activated to crimp and cut the suture using the instrument that has just been described above. Finally, the instrument is removed, leaving the crimped sleeve member closing securing the suture.

While the applicant refers to the example of gastrointestinal endocscopic surgery, it will be understood that the invention is not limited to just those applications. Applicant intends that the crimping instrument can be used in any situation where sutures are to be secured by a deformable sleeve and then cut.

The crimping instrument of the present invention is designed so that it is positionally operated with the cooperating stops allowing a number of safety designs to secure the crimper and adjust the sutures in the crimping sleeve with just the right amount of crimping force at just the right time. These cooperating stops can be adjusted for different sizes or types of crimping sleeves.

While the invention has been shown and described with particularity, it will be appreciated that various changes and modifications may suggest themselves to one having ordinary skill in the art upon being apprised of the present invention. It is intended to encompass all such changes and modifications as they fall within the scope and spirit of the appended claims.

The invention claimed is:

1. An instrument for crimping a sleeve to a surgical suture comprising:
   (a) an anvil;
   (b) a hammer movable relative to the anvil for crimping a sleeve therebetween:
   (c) a pusher for engaging one of the hammer and anvil and relatively moveable for urging the hammer and the anvil together as the pusher moves longitudinally from a first position to a second position, the pusher also comprising a cutting blade for cutting a suture; and
   (d) cooperating stops adjacent to the hammer and the anvil for limiting the relative movement of the hammer and the anvil to control the amount of crimp.

2. The instrument of claim 1 in which the cooperating stops prevent further relative movement of the hammer and the anvil after the pusher reaches an intermediate position between the first position and the second position.

3. The instrument of claim 1 in which the blade cuts the suture as the pusher moves between the intermediate position and the second position.

4. The instrument of claim 2 in which the hammer and anvil comprise a resilient member comprising two opposed legs, the hammer is located near an end of one leg, and the anvil located near the end of die other leg, the member resiliently biasing the hammer and anvil apart in a normal configuration.

5. The instrument of claim 4 in which the pusher engages at least one of the first and second legs and urges them together to bring the hammer and anvil into opposition and to crimp a sleeve disposed therebetween.

6. The instrument of claim 1 in which the blade is effective to cut the suture as the pusher moves between the intermediate position and the second position.

7. The instrument of claim 1 in which the hammer and the anvil comprise a resilient member comprising two opposed legs, the hammer located at an end of one leg, and the anvil located at the end of the other leg, the member resiliently biasing the hammer and anvil apart in a normal configuration.

8. The instrument of claim 7 in which the pusher engages at least one of the first and second legs and urges them together to bring the hammer and anvil into opposition and to crimp a sleeve disposed therebetween.

9. The instrument of claim 8 in which the blade is effective to cut the suture as the pusher moves between the first position and the second position.

10. The instrument of claim 1 further comprising a second pair of cooperating stops adjacent to the hammer and the anvil, the anvil and hammer being disposed between the first and second pairs of stops.

11. The instrument of claim 10 in which the second pair of cooperating stops engage the suture therebetween.

12. The instrument of claim 7 in which the resilient member comprises an opening in one or the first and second legs for passing a suture therethrough.

13. The instrument of claim 12 in which the cutter is disposed on the opposite side of the opening from the sleeve.

14. The instrument of claim 1 such that the stops are both on one of the anvil or the hammer.

15. The instrument of claim 14 in which the hammer and the anvil comprise a resilient member comprising two opposed legs, the hammer located at an end of one leg, and the anvil located at the end of the other leg, the member resiliently biasing the hammer and anvil apart in a normalt configuration.

16. The instrument of claim 15 in which the pusher engages at least one of the first and second legs and urges them together to bring the hammer and anvil into opposition and to crimp a sleeve disposed therebetween.

17. The instrument of claim 16 in which the pusher engages at least one of the first and second legs and urges them together to bring the hammer and anvil into opposition and to crimp a sleeve disposed therebetween.

18. The instrument of claim 17 in which a blade is effective to cut the suture as the pusher moves between the first position and thesecond position.

19. The instrument of claim 18 in which the resilient ri,ember comprises an opening in one or the first and second legs for passing a suture therethrough.

20. The instrument of claim 19 in which a cutter is disposed on the opposite side of the opening from the sleeve.

21. An instrument for crimping a sleeve to a surgical suture comprising:
   (a) an anvil;
   (b) a hammer there between;
   (c) a pusher having two legs for engaging one of the hammer and the anvil and relatively moveable for urging the hammer and the anvil together as the pusher moves longitudinally from a first position to a second position; and
   (d) cooperating stops adjacent to the hammer and the anvil for limiting the relative movement of the hammer and the anvil to control the amount of crimp in which the cooperating stops prevent further relative movement of the hammer and the anvil after the pusher reaches an intermediate position between the first position and the second position.

22. The instrument of claim 21 in which the cooperating stops engage the suture therebetween.

23. The instrument of claim 21 wherein the cooperating stops include one stop is hookshaped.

24. The instrument of claim 21 wherein the cooperating stops include a stop that is a protrusion.

25. The instrument of claim 21 wherein one leg has a sharp cutting edge.

26. The instrument of claim 21 wherein one leg has a blunt portion.

27. The instrument of claim 21 wherein the hammer and anvil together form a resilient ushaped crimper.

28. The instrument of claim 27 wherein the crimper is held in the instrument by a pin.

29. The instrument of claim 21 wherein the anvil further defines a seat for a cutting edge.

30. The instrument of claim 21 comprising a second stop and wherein the hammer flexes to engage the second stop after the first stop is engaged.

31. The instrument of claim 30 in combination with a sleeve wherein the first stop is closer to the sleeve than the second stop.

32. The instrument of claim 30 in combination with a sleeve wherein the second stop is closer to the sleeve then the first stop.

* * * * *